(12) United States Patent
Pi et al.

(10) Patent No.: US 10,499,821 B2
(45) Date of Patent: Dec. 10, 2019

(54) OPTICAL HEART RATE SENSOR

(71) Applicant: Shenzhen Goodix Technology Co., Ltd., Shenzhen (CN)

(72) Inventors: Bo Pi, Carlsbad, CA (US); Yi He, San Diego, CA (US)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 14/807,511

(22) Filed: Jul. 23, 2015

(65) Prior Publication Data
US 2016/0022160 A1    Jan. 28, 2016

Related U.S. Application Data (60) Provisional application No. 62/028,206, filed on Jul. 23, 2014.

(51) Int. Cl.
*A61B 5/00* (2006.01)
*A61B 5/024* (2006.01)
(Continued)

(52) U.S. Cl.
CPC ........ *A61B 5/02444* (2013.01); *A61B 5/0059* (2013.01); *A61B 5/0261* (2013.01);
(Continued)

(58) Field of Classification Search
CPC . A61B 5/0059; A61B 5/02444; A61B 5/0261; A61B 5/6898; A61B 5/7207; A61B 5/7225
See application file for complete search history.

(56) References Cited

U.S. PATENT DOCUMENTS

| | | | |
|---|---|---|---|
| 4,258,719 A | 3/1981 | Lewyn | |
| 6,611,704 B1 * | 8/2003 | van Best | A61B 5/0059 600/476 |

(Continued)

FOREIGN PATENT DOCUMENTS

| | | |
|---|---|---|
| CN | 103096792 A | 5/2013 |
| CN | 103605504 A | 2/2014 |

(Continued)

OTHER PUBLICATIONS

International Search Report and Written Opinion mailed on Oct. 13, 2015 for International Application No. PCT/US2015/041801, filed on Jul. 23, 2015 (8 pages).

(Continued)

*Primary Examiner* — Mark D Remaly
(74) *Attorney, Agent, or Firm* — Perkins Coie LLP (57) ABSTRACT

Techniques, systems and apparatus are described for implementing a heart rate sensor based on optical measurements of color response of human blood. An optical heart rate sensor can include light source circuitry including a first light emitting diode (LED) to output a first source light signal to a target measurement site, a second LED to output a second source light signal to the target measurement site, a first current pulse driver communicatively coupled to the first LED to modulate the first source light signal output from the first LED at a first predetermined frequency and a second current pulse driver communicatively coupled to the second LED to modulate the second source light signal output from the second LED at a second predetermined frequency different from the first predetermined frequency. The optical heart rate sensor can include detector circuitry including a light detecting photodiode connected to a bias voltage.

17 Claims, 12 Drawing Sheets

(51) Int. Cl.
*A61B 5/026* (2006.01)
*A61B 5/0295* (2006.01)
*A61B 5/1455* (2006.01)

(52) U.S. Cl.
CPC ........ *A61B 5/02416* (2013.01); *A61B 5/6898* (2013.01); *A61B 5/7214* (2013.01); *A61B 5/7225* (2013.01); *A61B 5/7228* (2013.01); *A61B 5/0295* (2013.01); *A61B 5/14551* (2013.01); *A61B 5/14552* (2013.01); *A61B 5/7207* (2013.01); *A61B 5/7242* (2013.01); *A61B 2560/0233* (2013.01); *A61B 2560/0247* (2013.01); *A61B 2562/0238* (2013.01); *A61B 2562/04* (2013.01)

(56) References Cited

U.S. PATENT DOCUMENTS

| | | | |
|---|---|---|---|
| 6,731,967 | B1 | 5/2004 | Turcott |
| 7,751,595 | B2 | 7/2010 | Russo |
| 8,283,620 | B2 | 10/2012 | Raynor et al. |
| 8,725,842 | B1 | 5/2014 | Al-Nasser |
| 2005/0038344 | A1 | 2/2005 | Chance |
| 2009/0309645 | A1 | 12/2009 | Isaacson et al. |
| 2011/0137181 | A1 | 6/2011 | Lin et al. |
| 2013/0194066 | A1 | 8/2013 | Rahman et al. |
| 2013/0201049 | A1 | 8/2013 | Sugimoto |
| 2014/0127996 | A1 | 5/2014 | Park et al. |
| 2016/0179197 | A1 | 6/2016 | Qian et al. |
| 2016/0224816 | A1 | 8/2016 | Smith et al. |

FOREIGN PATENT DOCUMENTS

| | | |
|---|---|---|
| CN | 103870220 A | 6/2014 |
| CN | 103876714 A | 6/2014 |

OTHER PUBLICATIONS

European Search Report from corresponding European Patent Application No. 15825544.8 dated Jul. 5, 2017, (9 pages).

Tavakoli et al. "An Ultra-Low-Power Pulse Oximeter Implemented With an Energy-Efficient Transimpedance Amplifier" IEEE Transactions on Biomedical Circuits and Systems, (2010), vol. 4, No. 1, pp. 27-38.

Article 94(3) EPC issued on May 22, 2018, in corresponding European Patent Application No. 15825544.8 (8 pages).

Office Action Mailed in Chinese Application No. 201580023898.7 dated Jul. 8, 2019.

Examination Report dated Oct. 1, 2019 for Indian Patent Application No. 201617041995, filed Dec. 8, 2016 (8 pages).

\* cited by examiner

OPTICAL HEART RATE SENSOR

CROSS REFERENCE TO RELATED APPLICATIONS

This patent document claims the benefit of priority of U.S. Provisional Patent Application No. 62/028,206, filed on Jul. 23, 2014. The entire contents of the before-mentioned patent applications are incorporated by reference as part of the disclosure of this document.

BACKGROUND

This application relates to devices, techniques and systems for detecting heart rates using an optical sensor.

In a typical optical heart rate sensor, a photodiode, a low noise amplifier and an analog to digital converter (ADC) can be used to measure the photodiode response with a LED with different wavelength as light source. The sensitivity of the optical sensor to background light and motion of the user can cause significant interferences of measurements. The low noise amplifier usual requires more power, and the useful heart rate signals usually is only 100th to 10,000th of the total photodiode signals.

SUMMARY

Techniques, systems and apparatus are described for implementing a heart rate sensor based on optical measurements of color response of human blood. The described heart rate sensor can be integrated into a portable device such as a smart watch to provide continuous sensing of a user's heart rate and to provide a combined sensor data in tandem with one or more other sensors including a motion sensor and another biometric sensor such as a blood pressure sensor and a blood oxygen sensor. The collected heart rate sensor data can be combined with and correlated with other sensor data and uploaded to a cloud server to provide relevant user feedback, perform statistical analysis and create cloud based services (e.g. sensor ratings) based on the collected combined sensor data.

In one aspect, an optical heart rate sensor is disclosed. The optical heart rate sensor includes light source circuitry. The light source circuitry includes a light emitting diode (LED) to output a source light signal to a target measurement site, and a current pulse driver communicatively coupled to the LED to modulate the source light signal output from the LED at a predetermined frequency. The optical heart rate sensor includes detector circuitry. The detector circuitry includes a light detecting photodiode connected to a bias voltage. The light detecting photodiode can generate a detector current responsive to detecting a target light signal reflected or scattered from the target measurement site in response to the modulated light signal. The detector circuitry includes a bank of switches communicatively coupled to the photodiode, and a capacitor communicatively coupled to the bank of switches. The bank of switches can switch on and off in response to pulse signals in opposite phases to generate an integrator signal based on charges integrated on the capacitor by the generated detector current.

The optical heart rate sensor can be implemented in various ways to include one or more of the following features. The bank of switches can switch on and off in response to pulse signals in opposite phases to generate the integrator signal to alternately integrate a charge in the capacitor in opposite directions. The integrator signal can be used to cancel out a background light signal present in the detector current. The integrator signal can be used to correlate to a heart rate.

In another aspect, an optical heart rate sensor is disclosed. The optical heart rate sensor includes light source circuitry. The light source circuitry includes a first light emitting diode (LED) to output a first source light signal to a target measurement site, a second LED to output a second source light signal to the target measurement site, a first current pulse driver communicatively coupled to the first LED to modulate the first source light signal output from the first LED at a first predetermined frequency and a second current pulse driver communicatively coupled to the second LED to modulate the second source light signal output from the second LED at a second predetermined frequency different from the first predetermined frequency. The optical heart rate sensor includes detector circuitry. The detector circuitry includes a light detecting photodiode connected to a bias voltage. The light detecting photodiode can generate a detector current responsive to detecting a target light signal reflected or scattered from the target measurement site in response to the modulated light signals. The detector circuitry includes a bank of switches communicatively coupled to the photodiode, and a capacitor communicatively coupled to the bank of switches. The bank of switches can switch on and off in response to pulse signals in opposite phases to allow the generated detector current from the light detecting photodiode to alternately integrate a charge in the capacitor in opposite directions. The bank of switches can switch on and off in response to pulse signals in opposite phases to generate the integrator signal based to alternately integrating a charge in the capacitor in opposite directions. The integrator signal can be used to cancel out a background light signal present in the detector current. The modulated light signals of different frequencies can be subtracted to compensate for motion artifacts. The integrator signal can be used to correlate to a heart rate.

In another aspect, an exemplary process for optically sensing a hear rate is disclosed. The process includes emitting, from a light source, a source light signal to a target measurement site. The process includes modulating, by a current pulse driver communicatively coupled to the light source, the source light signal emitted from the light source at a predetermined frequency. The process includes generating, from a light detecting photodiode, a detector current responsive to detecting a target light signal reflected or scattered from the target measurement site in response to the modulated light signal. The process includes generating an integrator signal based on the generated detector current.

The process can be implemented in various ways to include one or more of the following features. Generating the integrator signal can include switching on and off a bank of switches communicatively coupled to a capacitor in response to pulse signals in opposite phases. Switching on and off the bank of switches in response to the pulse signals in opposite phases to generate the integrator signal can include alternately integrating a charge in the capacitor in opposite directions. The integrator signal can be used to cancel out a background light signal present in the detector current. The integrator signal can be used to correlate to a heart rate. The process can include emitting, by another source light, another source light; and modulating, by another current pulse driver communicatively coupled to the other source light, the other source light signal emitted from the other light source at another predetermined frequency different from the predetermined frequency. The generating the detector current can include generating, from the light detecting photodiode, the detector current responsive to detecting a target light signal reflected or scattered from the target measurement site in response to the modulated light signal and the other modulated light signal; and generating an integrator signal based on the generated detector current. The modulated light signals of different frequencies can be subtracted to compensate for motion artifacts.

In another aspect, an optical heart rate sensor is disclosed. The optical heart rate sensor includes light emitting means for emitting a source light signal to a target measurement site. The optical heart rate sensor includes signal modulating means for modulating emitted the source light signal emitted from the light emitting means at a predetermined frequency. The optical heart rate sensor includes light detector means for generating a detector current responsive to detecting a target light signal reflected or scattered from the target measurement site in response to the modulated light signal. The optical heart rate sensor includes switching means for turning on and off electrical connection to a capacitor to allow the capacitor to accumulate charges.

The optical heart rate sensor can be implemented in various ways to include one or more of the following features. For example, the switching means can be configured to switch on and off the electrical connection to the capacitor in response to pulse signals in opposite phases to generate an integrator signal to alternately integrate a charge in the capacitor in opposite directions. Also, the integrator signal can be used to correlate to a heart rate.

BRIEF DESCRIPTION OF THE DRAWINGS

Like reference symbols and designations in the various drawings indicate like elements.

DETAILED DESCRIPTION

A heart rate sensor described in this document includes hardware and software necessary to obtain hear rate data from a user wearing the heart rate sensor as a part of a portable device such as a smart watch. The described heart rate sensor can continuously collect heart rate sensor data from the user and combine the heart rate sensor data with sensor data from other sensors to enhance the accuracy of the sensor data analysis and provide relevant feedback information to the user. In addition, the heart rate sensor is capable of pairing with an external personal portable device, such as a smartphone or tablet to correlate the collected sensor data with activities performed by the user on the paired device. The heart rate sensor can pair with the external personal portable device directly or through a host device, such as a smart watch that includes the heart rate sensor. Through the host device or the paired external personal portable device, the sensor data from the heart rate sensor can be transmitted to a cloud server to collect the heart rate sensor data, correlate with other sensor data from the same host device for further analysis and provide statistical analysis of the collected sensor data and correlation analysis data.

The heart rate sensor data can be combined with other sensor data including motion and other biometric sensors from the same host device to more accurately track health related activities (e.g., running, swimming, walking, etc.) to not only measure the extent of the user's motion but also the intensity of the user's motions during the activity. The heart rate sensor data can be combined with motion sensor data to identify activities that burn more calories, for example.

Similar to the health tracking application, the combined sensing of the motion and heart rate can be used to identify medically significant events, trigger sending of automated messages or warnings associated with the identified medically significant events, and take any appropriate actions.

Described below are various features of the described techniques, apparatus and systems and associated examples.

Light Absorption by Human Blood

Figure 1:
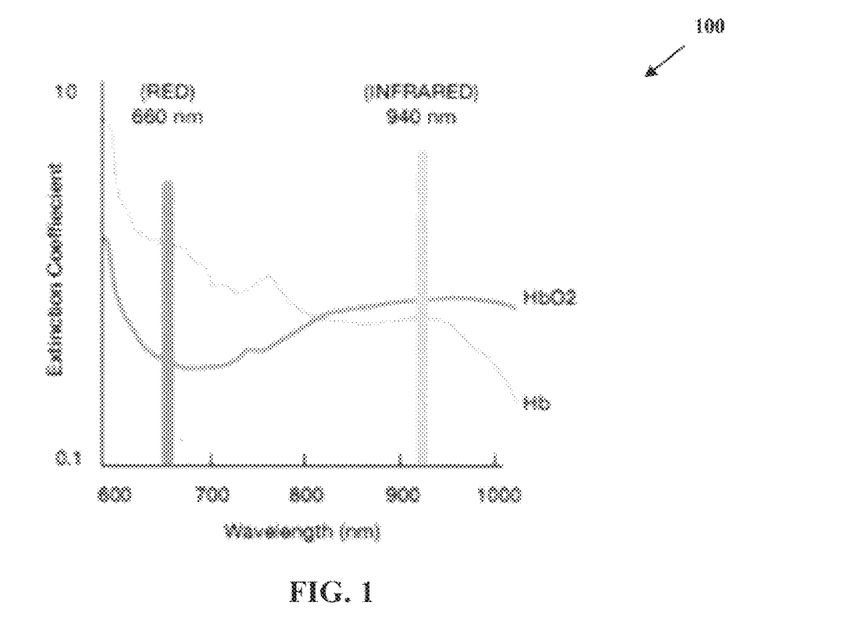
FIG. 1 shows exemplary absorption characteristics of human blood for absorbing different wavelengths of light.
Figure 2:
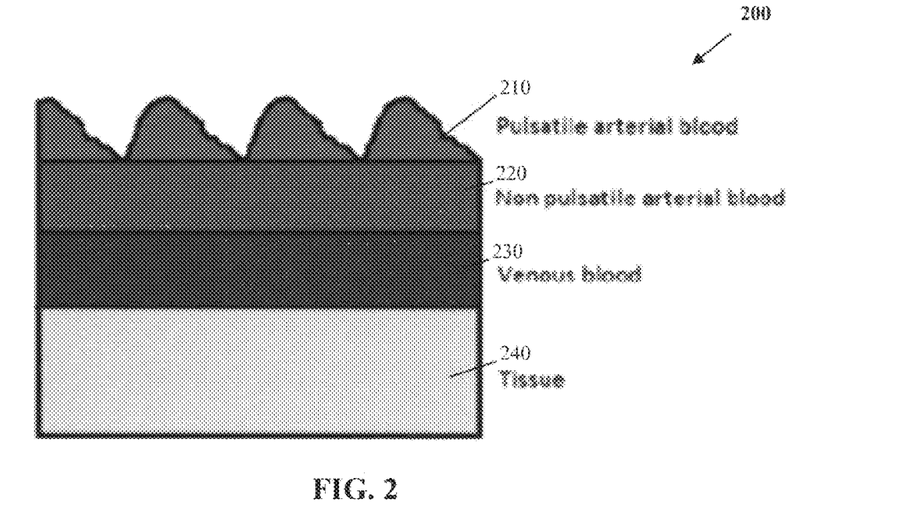
FIG. 2 is a graph showing exemplary light intensities of different wavelengths of light corresponding to blood in different phases of a heart beat cycle.

An optical heart rate sensor measures the varied absorption of different wavelength of light by the human blood. FIG. 1 is a graph 100 showing exemplary absorption characteristics of human blood for absorbing different wavelengths of light. Factors that affect the light absorption characteristics of human blood include the different levels of oxygen saturation in the blood stream and the different phases of a heart beat or rate cycle. An optical heart rate sensor can measure the intensity of different wavelengths of light that pass or scatter back from human tissues to obtain a signal that closely track the heart beat cycle. FIG. 2 is a graph 200 showing exemplary light intensities of different wavelengths of light corresponding to blood in different phases of a heart beat cycle. Shown in FIG. 2 are the light intensities for pulsating arterial blood 210, non-pulsating arterial blood 220, venous blood 230, and tissue 240. Assuming all other conditions are equal (e.g., means, light direction, intensity, and detection efficiency all stay equal), different wavelengths of light should have different amplitudes. Based on these optical characteristics of human blood, the heart rate of a user can be accurately measured.

Figures 3A, 3B:
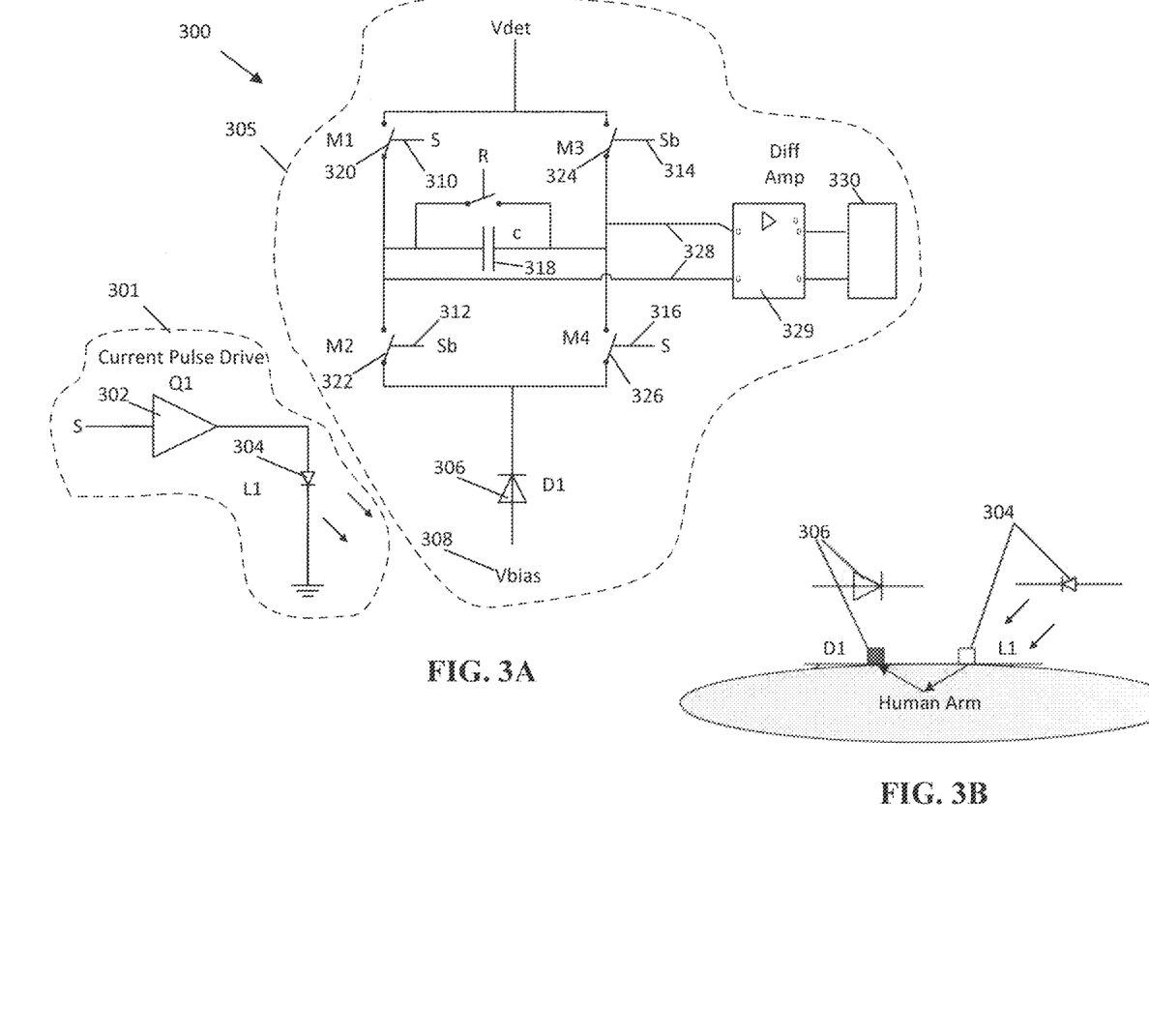
FIGS. 3A and 3B show an exemplary optical sensor for measuring heart rate.

FIGS. 3A and 3B show an exemplary optical sensor 300 for measuring heart rate. The optical sensor 300 can be particularly useful for measuring the human heart rate from a human finger or arm as the measurement site. The optical sensor 300 includes light source circuitry 301 and detector circuitry 305. The light source circuitry 301 includes a current pulse driver (Q1) 302, implemented using an op-amp for example, which can modulate light output signal from a light emitting diode (LED) (L1) 304 at a predetermined frequency. The LED (L1) 304 can be driven with on/off phases equally. The current pulse driver (Q1) 302 can use pulse signals (S) 310, 316 and ($S_b$) 312, 314 to modulate the light output signal from the LED (L1) 302.

The detector circuitry 305 includes a light detecting photodiode (D1) 306 connected to a bias voltage ($V_{bias}$) 308, a bank of switches (M1) 320, (M2) 322, (M3) 324, (M4) 326 and a capacitor (C) 318. The bank of switches (M1) 320, (M2) 322, (M3) 324, (M4) 326 is driven by pulse signals with opposite phases (S) 310, 316, and ($S_b$) 312, 314 to allow the photo current from the photodiode (D1) 306 to perform alternate charge integration of capacitor (C) 318 in opposite directions. In the presence of a background light signal which remains substantially constant or changes very slowly compared with a light signal of switching frequency, the alternate charge integration can be used to cancel out the background light signal. Since the light output signal from LED (L1) 304 is modulated by the same frequency and same phase of the integrator phase, the photo current from the photodiode (D1) 304 is added up with each switch cycle. Accordingly, the integrator signal increases with the increasing number of switch cycles. A differential amplifier 329 can amplify the integrator signal 328, and the output signal of the differential amplifier can be stored in a storage device 330.

Figure 4:
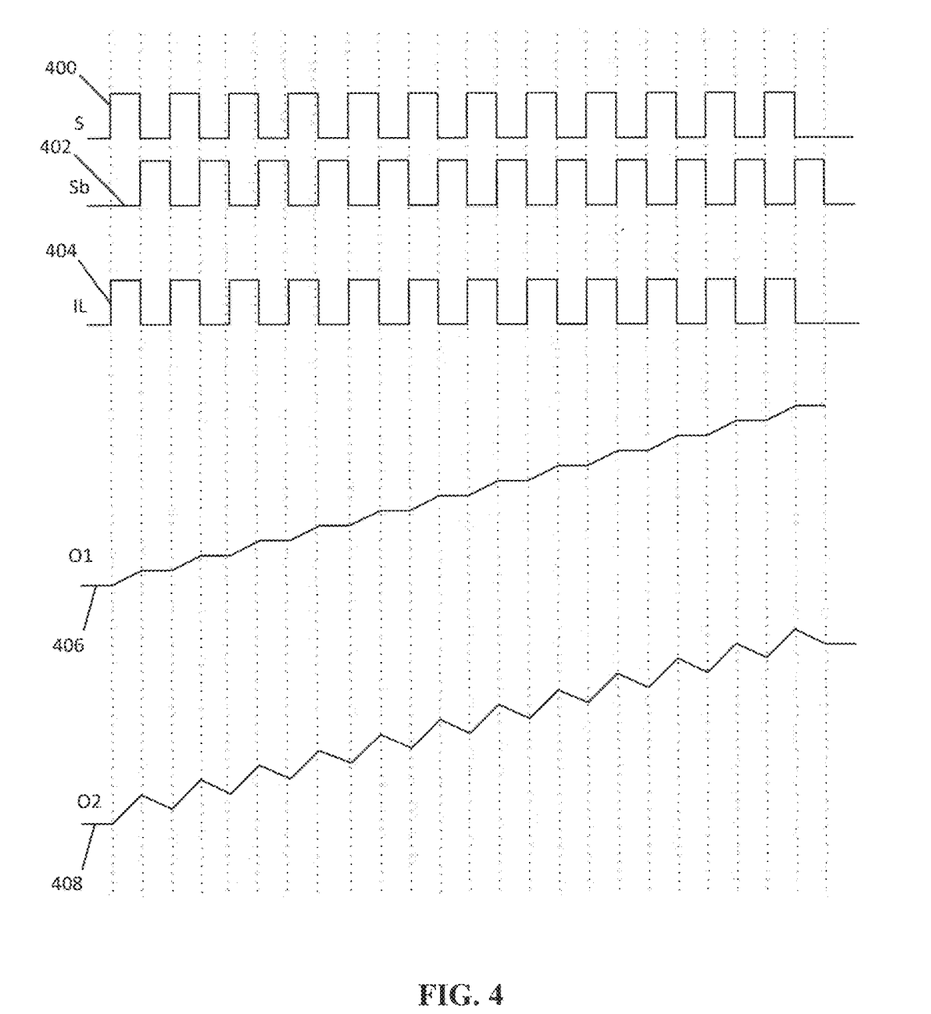
FIG. 4 shows exemplary signals from an optical heart rate sensor.

FIG. 4 shows exemplary signals from an optical heart rate sensor. Exemplary Pulse signals (S) 400 and ($S_b$) 402 of opposite phases drive a bank of switches (e.g., (M1) 320, (M2) 322, (M3) 324, (M4) 326 as shown in FIGS. 3A and 3B to allow the photo current from a photodiode (e.g., (D1) 306 from FIGS. 3A and 3B) to perform alternate charge integration of a capacitor (e.g., (C) 318 from FIGS. 3A and 3B) in opposite directions. The same pulse signal (S) 400 also modulate the light output signal (IL) 404 from an LED (e.g., (L) 304) that elicit the light reflected back from a human tissue and detected by the photodiode. In the absence of background light, the integrator signal (O1) 406 from the bank of switches connected to the capacitor increases continuously with each switch cycle. In the presence of a constant background light signal, the integrator signal (O2) 408 can be seen to seesaw up and down while the overall signal amplitude increases. The illustration of the integrator signals (O1) 406 and (O2) 408 in the absence and presence of background light respectively indicate that a substantially constant background light signal portion is added/subtracted with each switch cycle while the LED light signals are integrated linearly.

Figures 5A, 5B:
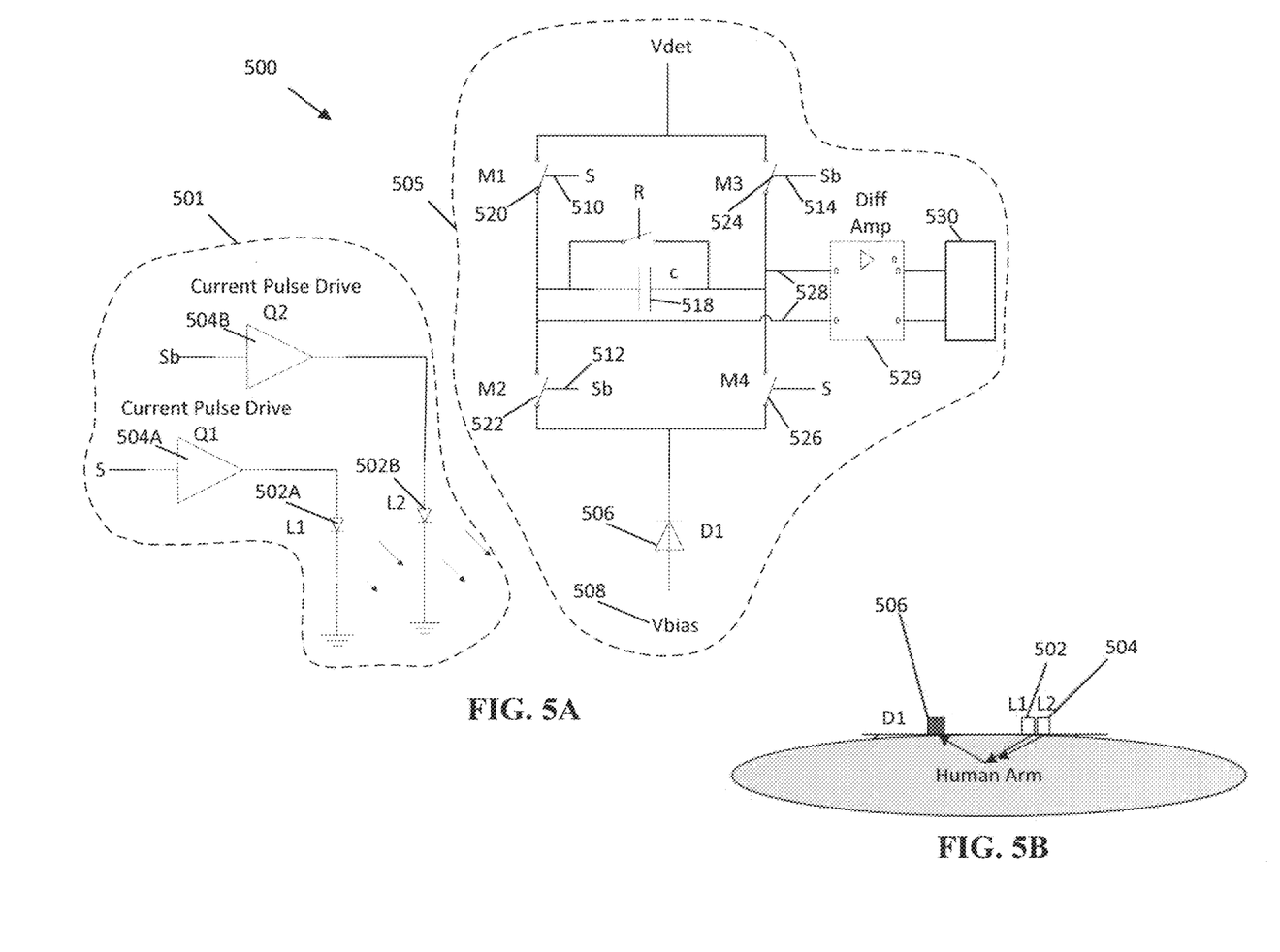
FIGS. 5A and 5B show an exemplary heart rate sensor configured to compensate for various interferences.

FIGS. 5A and 5B show an exemplary heart rate sensor configured to compensate for various interferences. In a typical measurement of the light signals incident on the human arm, the useful portion of the scattering light signals is approximately 1/1000 to 1/10000 of the total scattered light signals. Accordingly, the differential amplifier (e.g., differential amplifier 318) that amplify the integrator signal may have a very large dynamic range, which can reduce its usefulness. In addition, motion of the human arm being measured can cause the light scatter path to change. The large dynamic range of the differential amplifier and interference from the motion of the human arm can interfere with the ability of the optical heart rate sensor to accurately measure the heart beat signal.

To overcome or compensate for the above described issues, an enhanced optical heart rate sensor 500 can be implemented as illustrated in FIGS. 5A and 5B. Similar to the heart rate sensor 300 of FIGS. 3A and 3B, the enhanced heart rate sensor 500 includes light source circuitry 501 and detector circuitry 505. Unlike the optical heart rate sensor 300 of FIGS. 3A and 3B, the light source circuitry 501 of the enhanced optical heart rate sensor 500 includes two LEDs (L1) 502A and (L2) 502B configured to operate at two different wavelengths, each LED driven with independent pulse drive circuitry (Q1) 504A and (Q2) 504B. Each of the pulse drive circuitry (Q1) 504A and (Q2) 504B can produce the same pulse with opposite phases (180 degree differences). The two LEDs (L1) 502A and (L2) 502B are placed close together with an optional optical light mixer to ensure the light signals emitting out of the two LEDs (L1) 502A and (L2) 502B are mixed well before being directed to the human tissue of interest (e.g., the finger or the arm). The wavelengths of the two LEDs (L1) 502A and (L2) 502B can be chosen to have different absorptions by the human tissue of interest. For example, red (650 nm) and infrared (800-850 nm) light wavelengths can be chosen for the two LEDs (L1) 502A and (L2) 502B. The different light wavelengths can be chosen to reflect and associate with the significant differences in the absorption of light between blood with and without oxygen.

The detector circuitry 505 can be substantially similar to the detector circuitry 305. For example, the detector circuitry 505 includes a light detecting photodiode (D1) 506 connected to a bias voltage ($V_{bias}$) 508, a bank of switches (M1) 520, (M2) 522, (M3) 524, (M4) 526 and a capacitor (C) 518. The bank of switches (M1) 520, (M2) 522, (M3) 524, (M4) 526 is driven by pulse signals with opposite phases (S) 510, 516, and ($S_b$) 512, 514 to allow the photo current from the photodiode (D1) 506 to perform alternate charge integration of capacitor (C) 518 in opposite directions. A differential amplifier 529 can amplify the integrator signal 528, and the output signal of the differential amplifier can be stored in a storage device 530.

Figure 6:
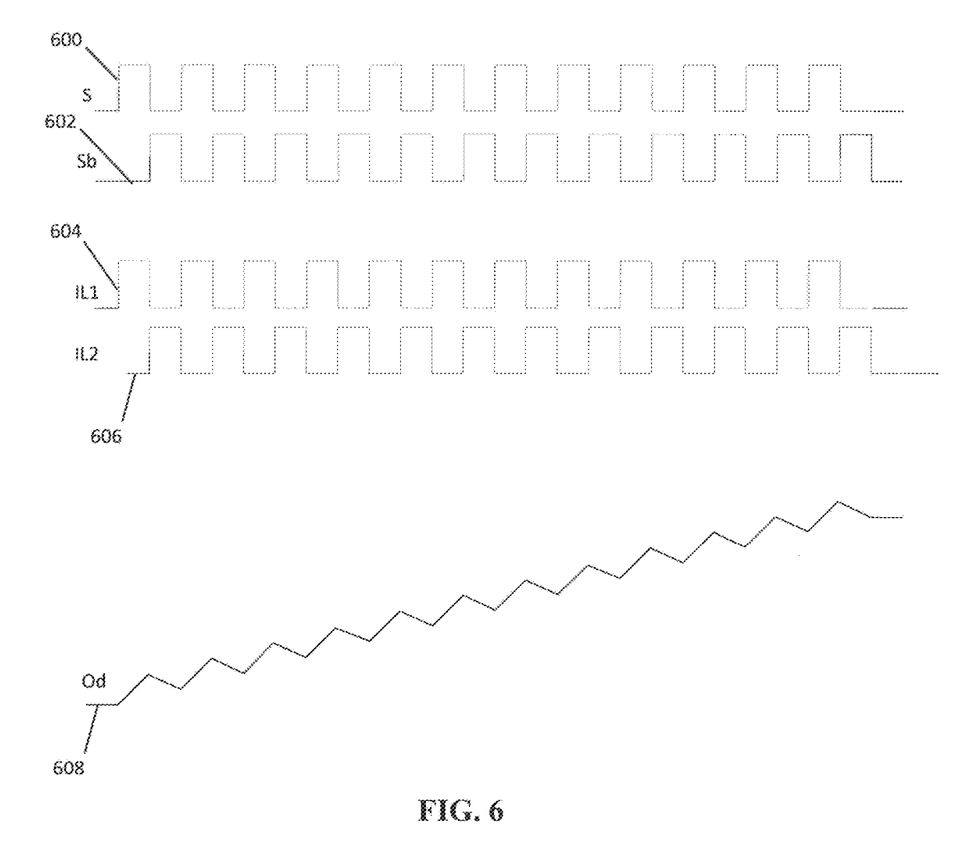
FIG. 6 shows exemplary signals from an enhanced optical heart rate sensor.

The detector circuitry 505 of FIGS. 5A and 5B can continue to integrate the photo current caused by the LEDs (L1) 502 and (L2) 504 and detected by the light detecting photodiode (D1) 506. Also, the detector circuitry 505 can subtract the signals between the two wavelengths of LEDs (L1) 502 and (L2) 504. The integrated and subtracted signal, the resultant signal, is free of background light as well, because the background light is a DC signal which is not in frequency or phase with the modulated signals from the LEDs (L1) 502 and (L2) 504. FIG. 6 below shows the resultant signal free from background signal.

FIG. 6 shows exemplary signals from an enhanced optical heart rate sensor. Exemplary pulse signals (S) 600 and ($S_b$) 602 of opposite phases drive a bank of switches (e.g., (M1) 520, (M2) 522, (M3) 524, (M4) 526 as shown in FIGS. 5A and 5B to allow the photo current from a photodiode (e.g., (D1) 506 from FIGS. 3A and 3B) to perform alternate charge integration of a capacitor (e.g., (C) 518 from FIGS. 5A and 5B) in opposite directions. The same pulse signals (S) 600 and ($S_b$) 602 also modulate the light output signals (IL1) 604 and (IL2) 606 from two LEDs (e.g., (L1) 502A and (L2) 502B that elicit the light signals at two different wavelengths reflected back from a human tissue and detected by the photodiode (D1) 506. In the presence of a constant background light signal, the integrator signal, the resultant signal (Od) 608 can be seen to be free of the substantially constant background light signal portion while the LED light signals are integrated linearly.

In addition, the resultant signal is correlated with the heart beat signal of the user because of the resultant signal corresponds to the different light absorption characteristics of the human blood at different phases of the heartbeat.

The resultant signal can potentially have several advantages. (1) The resultant signal has a relatively large portion (i.e., background signals are removed) correlated with heart beat signals. (2) The resultant signal is less sensitive to human motion artifacts because the two different wavelengths of the two LEDs go through relatively the same path during the human motion; thus the signals of the two wavelengths of the two LEDs change in sync with the motion. Subtraction of the two wavelength signals reduces the motion effect. (3) The pulse intensity of the two LEDs can be adjusted to maximize or enhance the signal correlation with the heat beat signal.

Figure 7A:
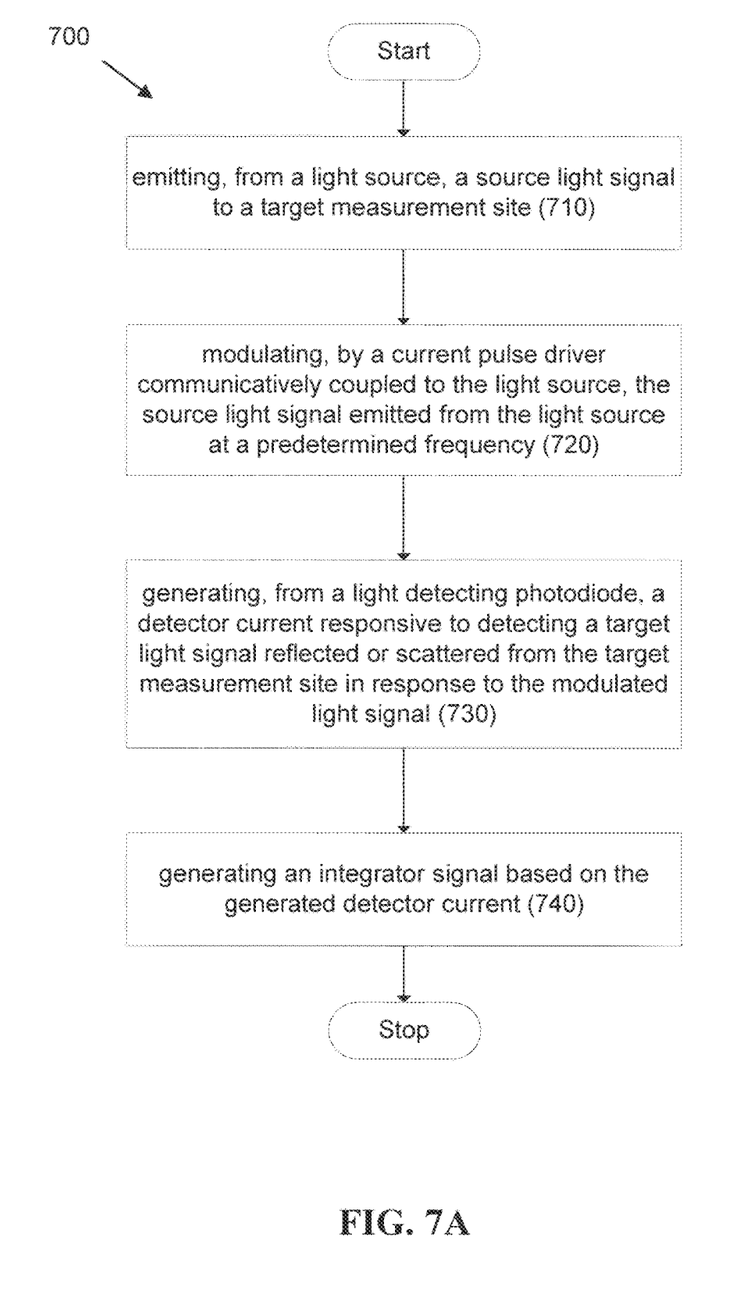
FIGS. 7A and 7B are process flow diagrams showing exemplary processes for optically sensing heart rate.
Figure 7B:
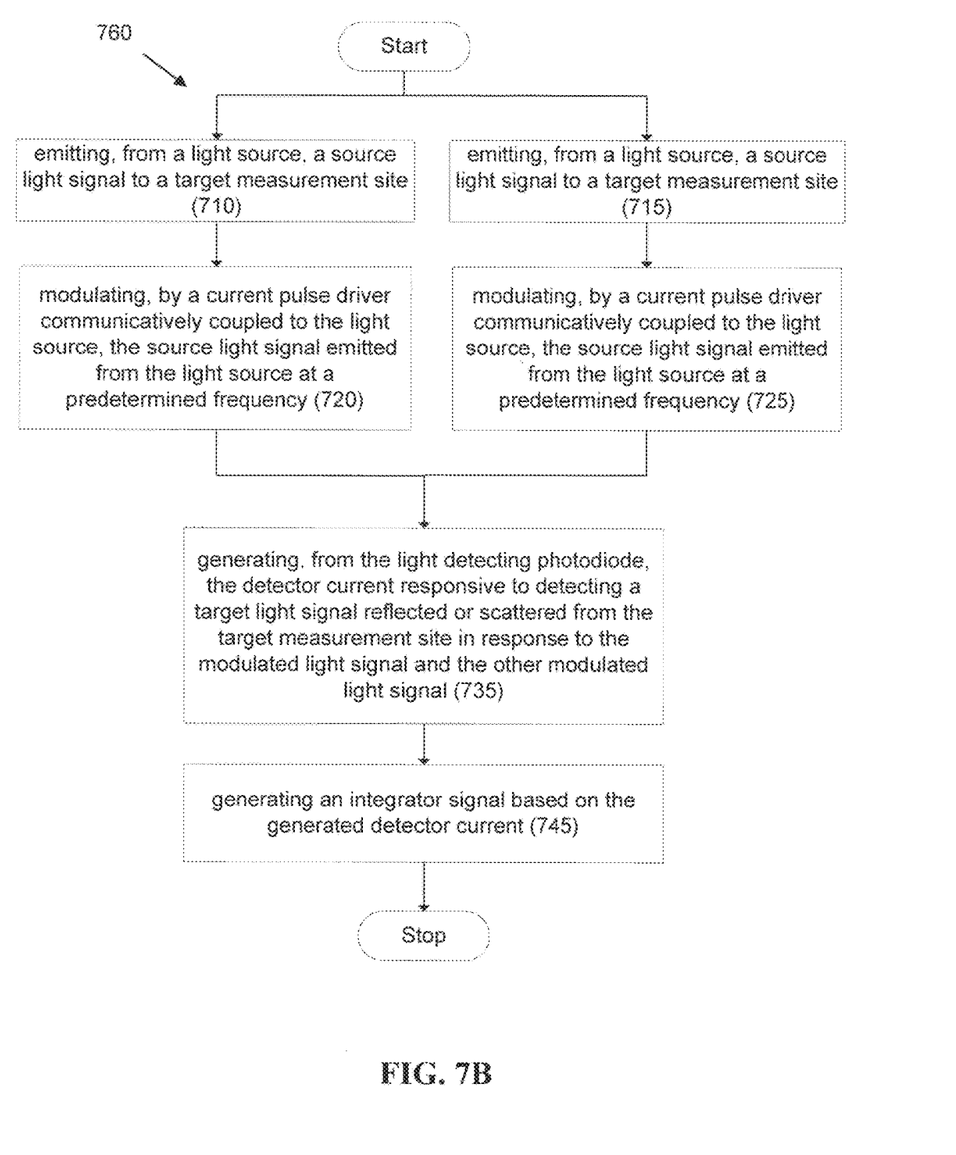

FIGS. 7A and 7B are process flow diagrams showing exemplary processes 700 and 760 for optically sensing a hear rate. The process 700 includes emitting, from a light source, a source light signal to a target measurement site (710). The process 700 includes modulating, by a current pulse driver communicatively coupled to the light source, the source light signal emitted from the light source at a predetermined frequency (720). The process 700 includes generating, from a light detecting photodiode, a detector current responsive to detecting a target light signal reflected or scattered from the target measurement site in response to the modulated light signal (730). The process 700 includes generating an integrator signal based on the generated detector current (740).

The process 700 can be implemented in various ways to include one or more of the following features. Generating the integrator signal can include switching on and off a bank of switches communicatively coupled to a capacitor in response to pulse signals in opposite phases. Switching on and off the bank of switches in response to the pulse signals in opposite phases to generate the integrator signal can include alternately integrating a charge in the capacitor in opposite directions. The integrator signal can be used to cancel out a background light signal present in the detector current. The integrator signal can be used to correlate to a heart rate. The process can include emitting, by another source light, another source light (715); and modulating, by another current pulse driver communicatively coupled to the other source light, the other source light signal emitted from the other light source at another predetermined frequency different from the predetermined frequency (725). The generating the detector current can include generating, from the light detecting photodiode, the detector current responsive to detecting a target light signal reflected or scattered from the target measurement site in response to the modulated light signal and the other modulated light signal (735); and generating an integrator signal based on the generated detector current (745). The modulated light signals of different frequencies can be subtracted to compensate for motion artifacts.

Sensor Applications

Figure 8:
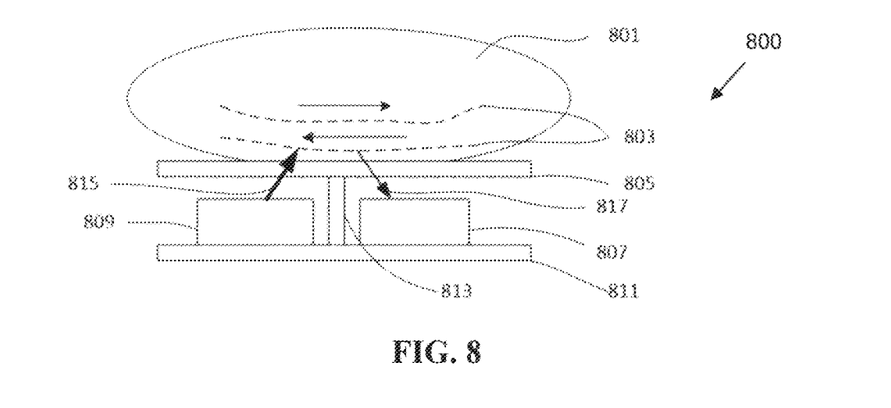
FIG. 8 is a block diagram showing an exemplary sensor configuration.

FIG. 8 is a block diagram showing an exemplary sensor 800 configuration. The sensor 800 can be implemented to be substantially similar to the sensors 300 or 500. The sensor 800 can include a light source 809 and a receiving photodetector array 807, such as photodiodes disposed over a substrate such as a packaging material 811. The light source 809 and the receiving photodetector array are isolated from each other by disposing a light blocker 813 between the light source 809 and the receiving photodetector array 807. The light blocker 813 blocks light beams 815 emitted from the light source 809 so that the emitted light beams do not reach the photodetector array 807 directly.

In some implementations, an optical window 805 is placed over the light source 809 and the receiving photodetector 807 to protect the light source 809 and the receiving photodetector 807. An object 801, such as a person's skin, to be monitored may touch the optical window 805 but will not touch the light source 809 and the receiving photodetector 807. The sensors 300, 500, and 800 can monitor the person's skin to detect the blood flow 803, which varies with the heartbeat, pressing force, breathing, and etc.

When the light beams 815 emitted from the light source 809 enters the object being monitored, the tissues in the object scatters a portion of the emitted light 815 as scattered light 817 into the receiving photodetector array 807. By analyzing the scattered light 817 received by the photodetector array 807, a sequence of information can be obtained.

The sensors 300, 500, and 800 can be used to perform blood monitoring to obtain a number of dynamic parameters. Examples of the dynamic parameters for blood monitoring can include heartbeat or heartrate, living organism detection, pressure force, vessel dynamic performances, and local blood flow velocity.

For example, as discussed above for FIGS. 1-2 and 8, the sensors 300, 500, and 800 can be used to perform heartrate or heartbeat monitoring. When the heart beats, the pulse pressure pumps the blood to flow in the arteries, so the extinction ratio of the object being monitored changes with the pulse. The scattered light signal received by the photodetector 807 carries the pulse information. The sensors 300, 500, and 800 can be implemented in a number of devices, such as a wrist watch, a head set, an ear set, or any other devices that can be worn by a person and contacts the person's skin.

Figure 9:
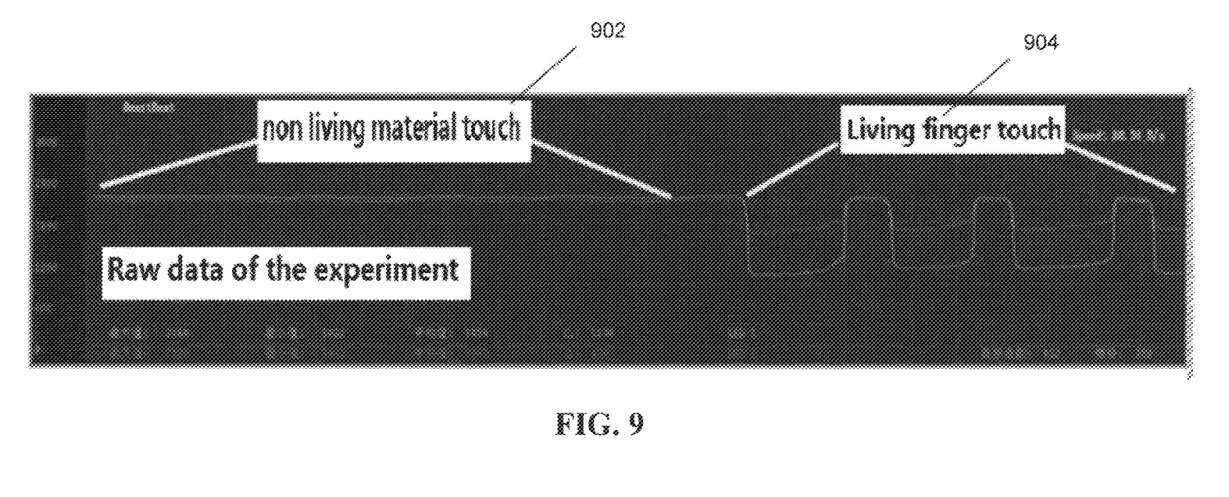
FIG. 9 is a diagram showing an exemplary living organism detection.

FIG. 9 is a diagram showing an exemplary living organism detection. The heartbeat sensor 300, 500, and 800 can be used to detect a living organism. Multiple light wavelengths are used to perform the living organism detection. FIG. 9 shows the results from a monitoring that uses two light sources. Each light source emits at different wavelengths.

When a non-living object touches the sensor, the received signal at the photodetector reveals pre-defined signal strength levels 902. When a living organism, such as a living finger touches the sensor, the received signal at the photodetector reveals signal strength levels 904 that are different from the pre-determined signal strength levels 902. The living finger induces the different signal strength levels that varies over time because the extinction ratios are different for different wavelengths. This detection technique for detecting a living organism can quickly determine whether the touching object is a living organism. In FIG. 9, the pulse-shaped signal reflects multiple touches rather than a blood pulse. Similar multiple touches with a non-living object does not show the same signal strength level as the living finger and rather maintains the predetermined signal levels.

Figure 10:
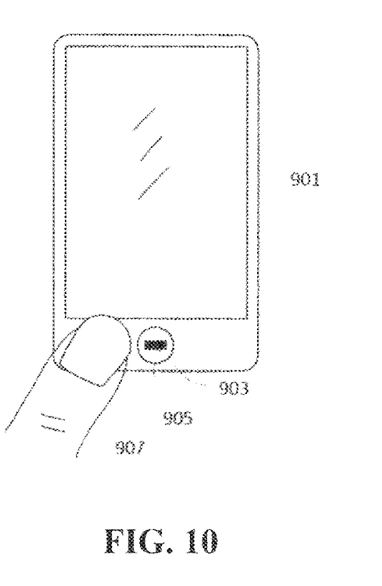
FIG. 10 is a block diagram showing an exemplary application of the living organism detection technique.

FIG. 10 is a block diagram showing an exemplary application of the living organism detection technique. The living organism detection can be implemented many applications, such as in mobile platform security enhancement. For example, a blood monitoring for living organism detection can be implemented in a mobile device 901, such as a smartphone. A sensor 903, which can be implemented substantially similar to sensors 300, 500, or 800 can be disposed in a home button 905 of the mobile device 901 or as a part of the touch screen assembly to detect whether an object 907 touching the sensor 903 is a living organism using the living organism detection described above. In some implementations, the sensor 903 can be installed in a military equipment issued to a soldier to determine the health condition of the soldier.

Figure 11:
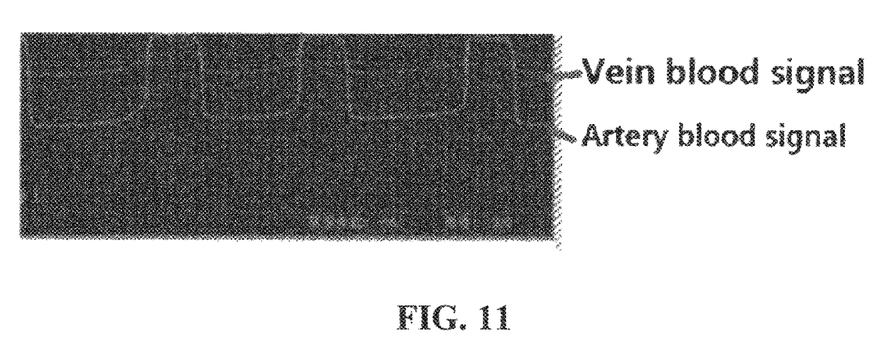
FIG. 11 is a diagram showing an exemplary pressure force monitoring.

FIG. 11 is a diagram showing an exemplary pressure force monitoring. A heartbeat sensor, such as sensor 300, 500, or 800 can be used to monitor a pressure force by using multiple wavelengths of light emitted by a light source. FIG. 11 shows the results of the pressure force monitoring using two light sources. Each light source emits at different wavelengths.

When a living finger touches the sensor, the signal received at the photodetector array reveals signal strength levels that are different from a touch from a non-living object because the extinction ratios are different for different wavelengths for a living object. In FIG. 11, the pulse-shaped signal reflects multiple touches rather than a blood pulse.

An increase in the pressure force applied by the living organism affects the blood flow in the arteries along with the signal amplitudes received at the photodetector array. With the increase of the pressure force, the signal amplitude difference between the arterial blood signal and the venous blood signal reduces. When the pressure force is strong enough, the arterial blood signal may become stronger than the venous blood signal. By comparing the signals, a calibration can be performed to detect the pressure force.

Figure 12:
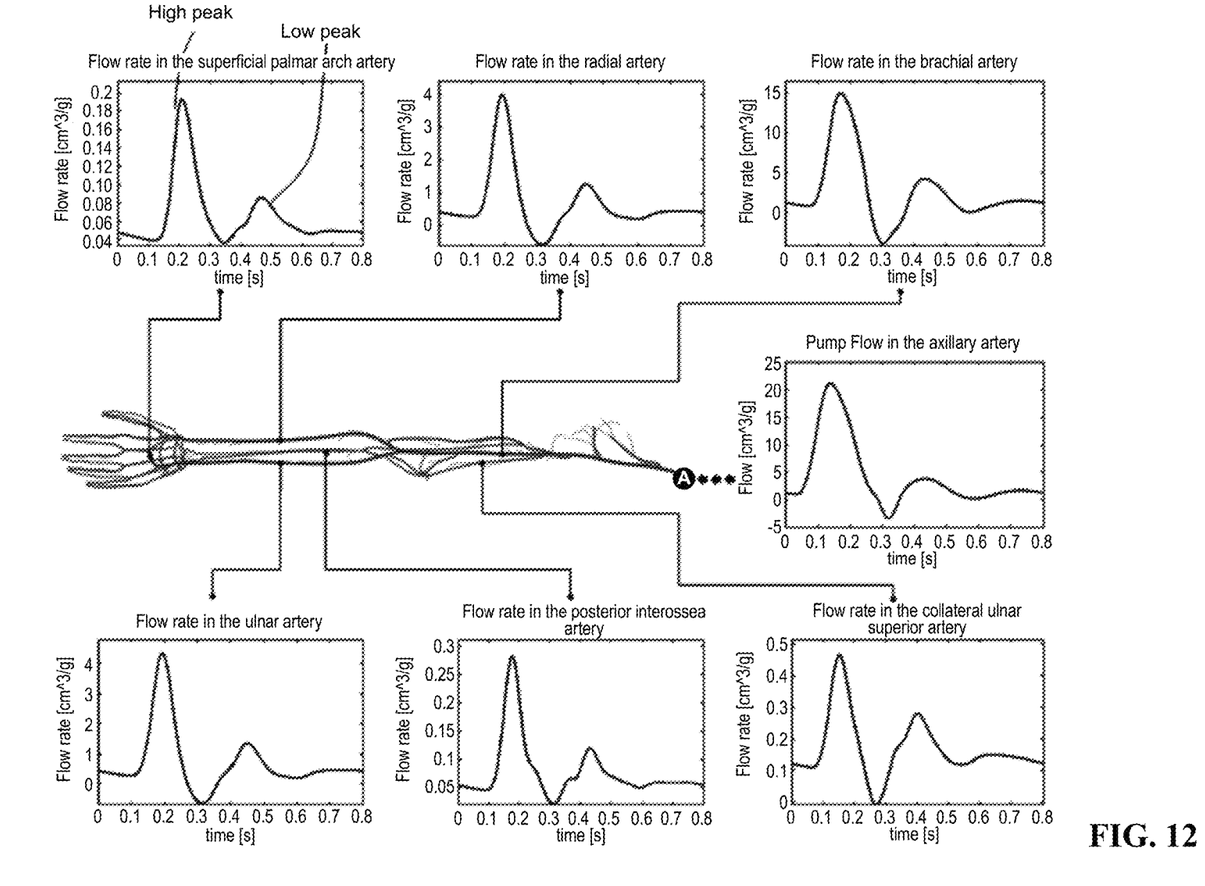
FIG. 12 is a collection of diagrams showing an exemplary blood flow performance monitoring indicating that a pulse profile differs for different vessels.

FIG. 12 is a collection of diagrams showing an exemplary blood flow performance monitoring indicating that a pulse profile differs for different vessels. The blood flow performance is strongly related to the health conditions of the person being monitored. The difference between the high peak and low peak reflects the quality of the blood flow system of the person, including the heart health condition and vessel performance.

Table 1 shows exemplary systolic velocity, typical velocity, and diastolic velocity for blood in different vessels.

| Name | Systolic velocity (cm/s) | Typical velocity (cm/s) | Diastolic velocity (cm/s) |
| --- | --- | --- | --- |
| Aorta | 100 | | |
| Brachial artery | | 50 | |
| Radial artery | 30 | | 20 |
| Ulnar artery | 30 | | 20 |
| Proper digital artery | | 10 | |
| Capillary artery | | 0.03–0.1 | |

Figure 13:
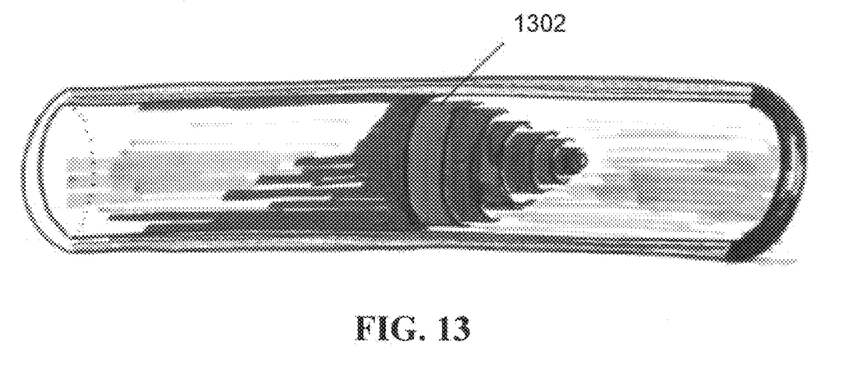
FIG. 13 is a diagram illustrating an exemplary blood flow velocity profile.

FIG. 13 is a diagram illustrating an exemplary blood flow velocity profile. The blood flow velocity at a center 1302 is higher than the other parts of the vessel. In a given artery, the blood flow velocity is proportional to the blood pressure. By using multiple heartbeat sensors, the local blood flow velocity can be detected and the blood pressure can be further monitored.

Figure 14:
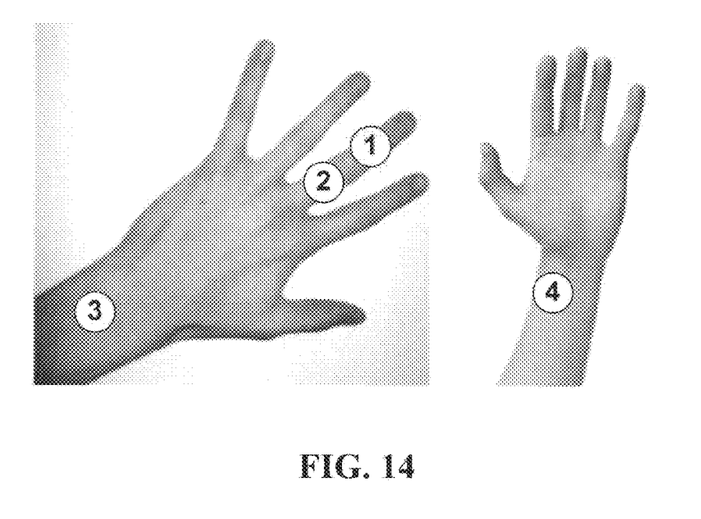
FIG. 14 is a diagram showing an exemplary blood flow performance monitoring, such as blood flow velocity monitoring.

FIG. 14 is a diagram showing an exemplary blood flow performance monitoring, such as blood flow velocity monitoring. For example, several locations on the hand can be used to touch the sensor and monitor the blood flow velocity. Exemplary locations include locations 1 and 2 over a finger. Other exemplary locations include locations 3 and 4 over the wrist radial artery, over the ulnar artery, over the ramus posterior artery, or over a capillary artery in the arm skin. By comparing the pulse time delay between any two locations, the blood flow velocity can be determined.

Figure 15:
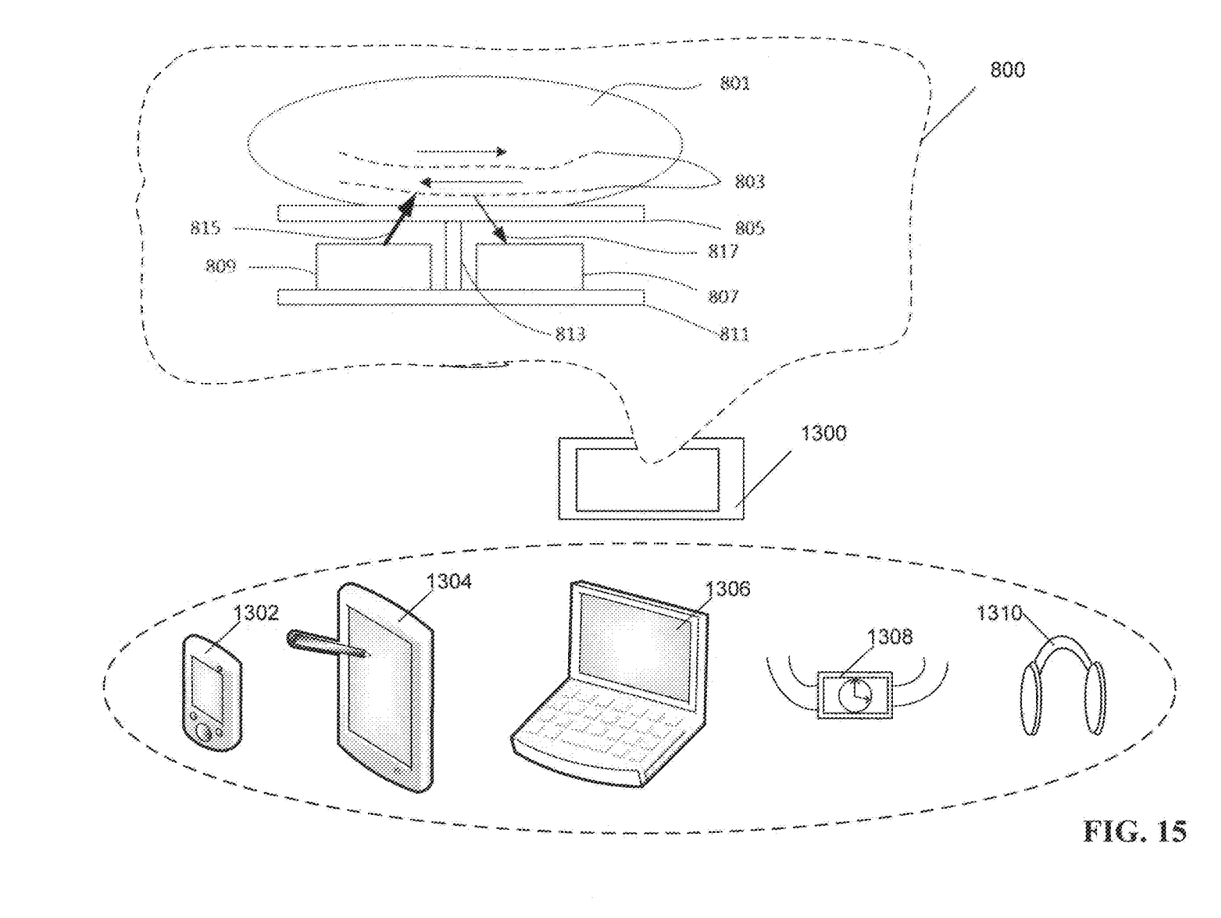
FIG. 15 is a high-level overview diagram showing exemplary end user devices for implementing a blood sensor as disclosed in this patent document.

FIG. 15 is a high-level overview diagram showing exemplary end user devices for implementing a blood sensor 300, 500, or 800 as disclosed in this patent document. The blood sensor 300, 500, or 800 can be implemented in an electronic device 1300 suitable for perform the various detection techniques disclosed in this patent document. Examples of the electronic device 1300 can include a mobile device 1302, such as a smartphone, a tablet computer 1304, a laptop 1306, a wearable device 1308, and an ear-phone 1310. The wearable device 1308 can include a smartwatch, an armband, a fitness tracker, and other similar device worn by a user.

While this document contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this document.

What is claimed is:

1. An optical heart rate sensor comprising:
   light source circuitry comprising:
      a light emitting diode (LED) to output a source light signal to a target measurement site, and
      a current pulse driver communicatively coupled to the LED to modulate the source light signal output from the LED on and off at a predetermined frequency; and
   detector circuitry comprising:
      a light detecting photodiode connected to a bias voltage, the light detecting photodiode configured to generate a detector current responsive to detecting, when the LED is on, a target light signal reflected or scattered from the target measurement site in response to the modulated light signal and a background light signal, and detecting, when the LED is off, the background light signal,
      a bank of switches communicatively coupled to the photodiode, and
      a capacitor communicatively coupled to the bank of switches,
   wherein the bank of switches is configured to switch on and off in response to pulse signals in opposite phases to generate an integrator signal representative of a difference between the target light signal in a phase and the background light signal in an opposite phase by integrating, for a plurality of cycles of the current pulse driver oscillating between the phase and the opposite phase at the predetermined frequency, charges in the capacitor in one direction for the phase and in the opposite direction for the opposite phase.

2. The optical heart rate sensor of claim 1, wherein the integrator signal is used to cancel out the background light signal present in the detector current.

3. The optical heart rate sensor of claim 1, wherein the integrator signal determines a heart rate.

4. The optical heart rate sensor of claim 1, wherein the charges integrated by the capacitor are representative of the target light signal when the LED is off subtracted from the target light signal when the LED is on.

5. An optical heart rate sensor comprising:
light source circuitry comprising:
  a first light emitting diode (LED) to output a first source light signal to a target measurement site,
  a second LED to output a second source light signal to the target measurement site, wherein a wavelength of the first light source is different from the second light source,
  a first current pulse driver communicatively coupled to the first LED to modulate the first source light signal output from the first LED at a predetermined frequency, and
  a second current pulse driver communicatively coupled to the second LED to modulate the second source light signal output from the second LED at the predetermined frequency,
  wherein during a phase, the first current pulse driver causes the first LED to be on and the second pulse driver causes the second LED to be off, and during an opposite phase, the first current pulse driver causes the first LED to be off and the second current pulse driver causes the second LED to be on; and
detector circuitry comprising:
  a light detecting photodiode connected to a bias voltage, the light detecting photodiode configured to generate a detector current responsive to the first LED during the phase and the second LED during the opposite phase,
  a bank of switches communicatively coupled to the photodiode, and
  a capacitor communicatively coupled to the bank of switches,
wherein the bank of switches is configured to cause the capacitor to integrate a difference signal between the detector current responsive to the first LED and the second LED.

6. The optical heart rate sensor of claim 5, wherein the bank of switches is configured to switch on and off in response to pulse signals in opposite phases to generate the difference signal by alternately integrating a charge in the capacitor in opposite directions.

7. The optical heart rate sensor of claim 5, wherein the difference signal cancels out a background light signal present in the detector current.

8. The optical heart rate sensor of claim 5, wherein the difference signal compensates for motion artifacts.

9. The optical heart rate sensor of claim 5, wherein the difference signal determines a heart rate.

10. A method of optically sensing a heart rate, the method comprising:
  emitting, from a light source, a source light signal to a target measurement site;
  modulating, by a current pulse driver communicatively coupled to the light source, the source light signal emitted from the light source at a predetermined frequency;
  generating, from a light detecting photodiode, a detector current responsive to detecting a target light signal reflected or scattered from the target measurement site in response to the modulated light signal; and
  generating an integrator signal representative of a difference between the source light signal in a phase and a background light signal in an opposite phase by integrating, for a plurality of cycles of the current pulse driver oscillating between the phase and the opposite phase at the predetermined frequency, charges in a capacitor in one direction for the phase and in the opposite direction for the opposite phase.

11. The method of claim 10, wherein the generating the integrator signal includes switching on and off a bank of switches communicatively coupled to a capacitor in response to pulse signals in opposite phases.

12. The method of claim 10, wherein switching on and off the bank of switches in response to the pulse signals in opposite phases to generate the integrator signal includes alternately integrating a charge in the capacitor in opposite directions.

13. The method of claim 10, wherein the integrator signal is used to cancel out a background light signal present in the detector current.

14. The method of claim 10, wherein the integrator signal can be used to correlate to a heart rate.

15. The method of claim 10, comprising:
  emitting, by another source light, another source light; and
  modulating, by another current pulse driver communicatively coupled to the other source light, the other source light signal emitted from the other light source at another predetermined frequency different from the predetermined frequency.

16. The method of claim 15, wherein the generating the detector current includes:
  generating, from the light detecting photodiode, the detector current responsive to detecting a target light signal reflected or scattered from the target measurement site in response to the modulated light signal and the other modulated light signal; and
  generating an integrator signal based on the generated detector current.

17. The method of claim 16, wherein the modulated light signals of different frequencies are subtracted to compensate for motion artifacts.

* * * * *